United States Patent [19]
Spencer

[11] Patent Number: 5,558,082
[45] Date of Patent: Sep. 24, 1996

[54] METHOD OF INTUBATING A PATIENT AND INTRODUCER FOR USE WITH SUCH METHOD

[76] Inventor: Robert F. Spencer, 22 Mountain View Dr., Waterbury, Vt. 05676

[21] Appl. No.: 369,819

[22] Filed: Jan. 9, 1995

[51] Int. Cl.⁶ .............................................. A61M 16/00
[52] U.S. Cl. .............................. 128/200.26; 128/207.14; 128/207.15; 128/205.23
[58] Field of Search ...................... 128/200.26, 207.14, 128/207.15, 205.23

[56] References Cited

U.S. PATENT DOCUMENTS

| | | | |
|---|---|---|---|
| 2,541,402 | 2/1951 | Caine | 128/200.26 |
| 3,503,385 | 3/1970 | Stevens . | |
| 3,802,440 | 4/1974 | Salem et al. . | |
| 4,329,983 | 5/1982 | Fletcher | 128/207.14 |
| 4,454,887 | 6/1984 | Krüger | 128/772 |
| 4,529,400 | 7/1985 | Scholten | 604/95 |
| 4,879,999 | 11/1989 | Leiman et al. | 128/207.14 |
| 4,938,746 | 7/1990 | Etheredge, III et al. | 604/265 |
| 5,054,500 | 10/1991 | Littleford et al. | 128/772 |
| 5,058,577 | 10/1991 | Six | 128/200.26 |
| 5,267,958 | 12/1993 | Buchbinder et al. | 604/96 |
| 5,279,285 | 1/1994 | Griggs | 128/200.26 |
| 5,375,592 | 12/1994 | Kirk et al. | 128/207.14 |
| 5,445,160 | 8/1995 | Culver et al. | 128/205.23 |

Primary Examiner—Aaron J. Lewis
Attorney, Agent, or Firm—Spencer & Frank

[57] ABSTRACT

A method of intubating a patient and an introducer for use with such method. The placement of the introducer is checked by measuring the carbon dioxide level of the gaseous medium flowing out of it, thereby giving an indication as to whether or not the introducer has been properly placed in the trachea of the patient. The introducer incorporates a flexible tube with a removable reinforcing element inside, which allows the introducer to be sufficiently stiff when being introduced into the patient and after removal of the reinforcing element, sufficiently flexible to be placed between the face of the patient and a face mask used to ventilate the patient.

13 Claims, 1 Drawing Sheet

METHOD OF INTUBATING A PATIENT AND INTRODUCER FOR USE WITH SUCH METHOD

BACKGROUND OF THE INVENTION

The present invention relates to a method of intubating a patient, particularly a patient to be anesthetized, and to an introducer for use with such method.

In the course of surgery or other medical procedures, it is commonly necessary to anesthetize the patient, and this frequently requires that the patient be ventilated during the procedure, such ventilation is achieved by way of an endotracheal tube. Endotracheal intubation, placement of a breathing tube into the trachea, is commonly performed after induction of general anesthesia to maintain a patent airway and prevent aspiration of oral secretions or stomach contents into a patient's lungs. Usually, the tube is passed through the mouth and into the trachea under direct vision of the larynx at the tracheal opening. A specialized flashlight or laryngoscope is used to hold the tongue and airway structures out of the way, including the epiglottis, a structure above the larynx that functions to prevent entrance of food and liquid into the lungs as we swallow. Individual variation in patients' anatomy occasionally makes it difficult to see past the epiglottis even with proper use of the laryngoscope.

If a difficult intubation is encountered, one of several accepted methods may be used to facilitate correct tube placement despite inability to directly view the opening to the trachea. One of these methods involves using an introducer as a guide. The most common introducers are long, non-hollow and flexible, yet malleable enough to hold a curved shape in one end. With the introducer threaded through an endotracheal tube, the curved end of the introducer is used to probe gently behind the epiglottis until the trachea is entered by feel rather than under direct vision. The endotracheal tube is then guided over the introducer and into the trachea. The introducer is then removed and the position of the endotracheal tube is confirmed by the usual methods.

A common risk associated with introducer assisted difficult intubations is inadvertent esophageal placement of the endotracheal tube. Esophageal intubation itself, recognized and quickly corrected, is not likely to harm the patient. However, there exists the possibility of gastric distention, vomiting, and aspiration after attempts to ventilate through a tube placed in the esophagus. Also there may be a delay in providing adequate ventilation to the lungs. If one could reliably confirm that the introducer is in the trachea rather than the esophagus before passing the endotracheal tube over the introducer, these risks could be avoided.

One way to confirm tracheal rather than esophageal placement of an introducer, is sample gas through a hollow lumen from holes drilled in the side of the introducer near its curved tip. With rare exceptions carbon dioxide is present in exhaled gasses sampled from the trachea but not in the esophagus. This distinction is commonly used to confirm correct tracheal placement after an endotracheal tube has been placed, by whatever means, by measuring the amount of carbon dioxide in gas sampled through the tube. It thus became possible to distinguish tracheal from esophageal placement of an introducer by measuring carbon dioxide sampled through the hollow lumen of the introducer. However, reliance of this method in clinical practice is questionable because what was sampled was tracheal gas from introducers that were passed into the trachea through a previously placed endotracheal tube. In clinical practice, the position of the introducer would need to be confirmed before the endotracheal tube would be placed.

Hollow lumen tubes which are similar in size and shape to conventional introducers are available and are used for other purposes. One such tube is marketed as Jet Stylet or Endotracheal Tube Changer. This device is used when removing or changing a previously placed endotracheal tube when there is concern about the possibility of a difficult re-intubation. The Jet Stylet is placed into the Trachea through the lumen of a previously placed endotracheal tube. The tube is then withdrawn over the stylet and removed while the stylet remains in the trachea. If re-intubation is required, a new tube can then be placed over the stylet and into the trachea (using the stylet exactly as one would use an introducer that is already correctly placed in the trachea). A significant benefit of a Jet Stylet is the ability to give oxygen to the patients lungs through the hollow lumen if necessary. The term Jet Stylet is used because high pressure oxygenation through a small lumen catheter is known as jet ventilation and is one alternative that can be used when normal endotracheal intubation cannot be accomplished.

It will be seen from the above that even skilled anesthesiologists will at times be uncertain as to whether the introducer has in fact been placed into the trachea rather than the esophagus, and it is, therefore, the object of the present invention to provide a way of making certain that first the introducer, and ultimately the endotracheal tube, is in fact properly positioned in the patient's trachea rather than in his or her esophagus.

BRIEF DESCRIPTION OF THE INVENTION

In accordance with the present invention, the above object is achieved by measuring the carbo dioxide content of the gas flowing out of the patient through the introducer. This will give an indication as to whether the end of the introducer has been placed into the trachea or into the esophagus, because the carbon dioxide measurement will be greater if the gas comes from the patient's lungs through the trachea than from the patient's esophagus.

To allow the above method to be carried out in an efficacious manner, the present invention further provides an introducer for facilitating the placement of an endotracheal tube into the trachea of the patient, namely, an introducer incorporating a flexible tube and a removable stiffening element, so that when the stiffening element is in the tube, the introducer as a whole has the desired stiffness, whereas with the stiffening element removed, the remaining tube is sufficiently flexible to allow the introducer to be placed between the face of the patient and a face mask that is in contact with the face of the patient.

DETAILED DESCRIPTION OF THE PREFERRED EMBODIMENT

Figure 1:
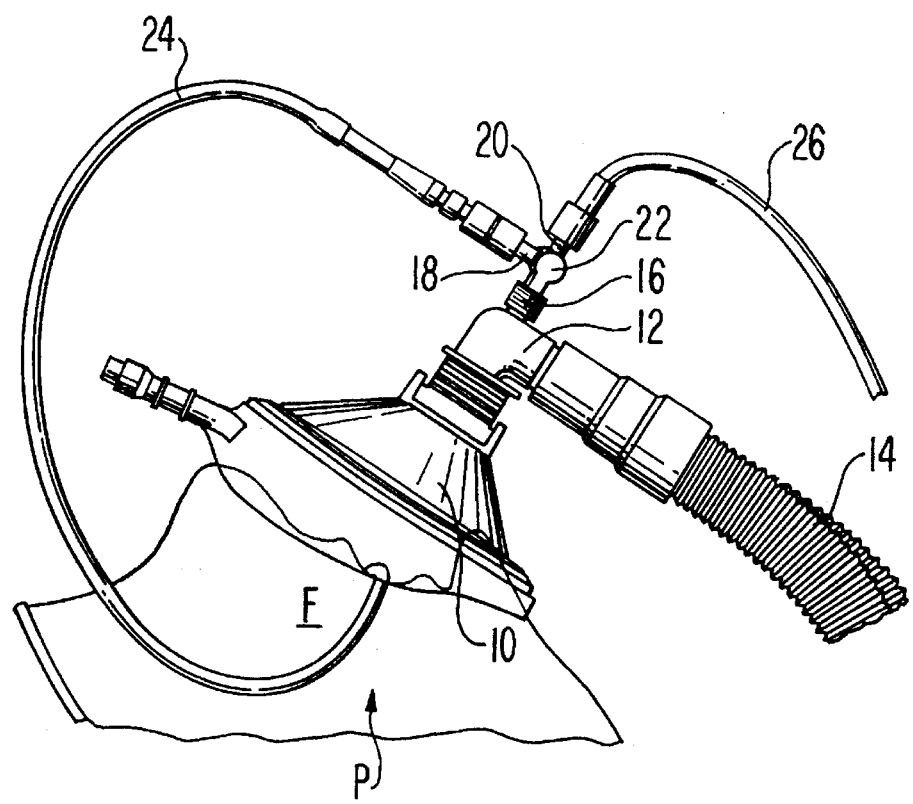
FIG. 1 is a schematic illustration of a patient whose face is covered by a face mask.

Referring now to the drawings, FIG. 1 shows the face F of patent P covered by a conventional ventilating mask 10 which has a stud 12 connected to hoses 14 leading a ventilator (not shown) for ventilating the patient during the procedure. The face mask 10 has a channel 16 which has two studs 18 and 20 as well as a three-way stop-cock or valve 22 which allows gas to flow from channel 16 to stud 20 or from stud 18 to stud 20. Stud 18 is connected to an introducer 24 which passes between the face mask 10 and the face of the patient. The stud 20 is connected to a hose 26 which is a sampling line leading to a capnograph (not shown) for measuring and displaying the levels of carbon dioxide content in the gas being sampled.

In one of the positions of the valve 22, gas flows from the mask 10 directly to the sampling line 26 leading to the capnograph and in the other position, gas flows to the capnograph from the introducer 24.

Figure 2:
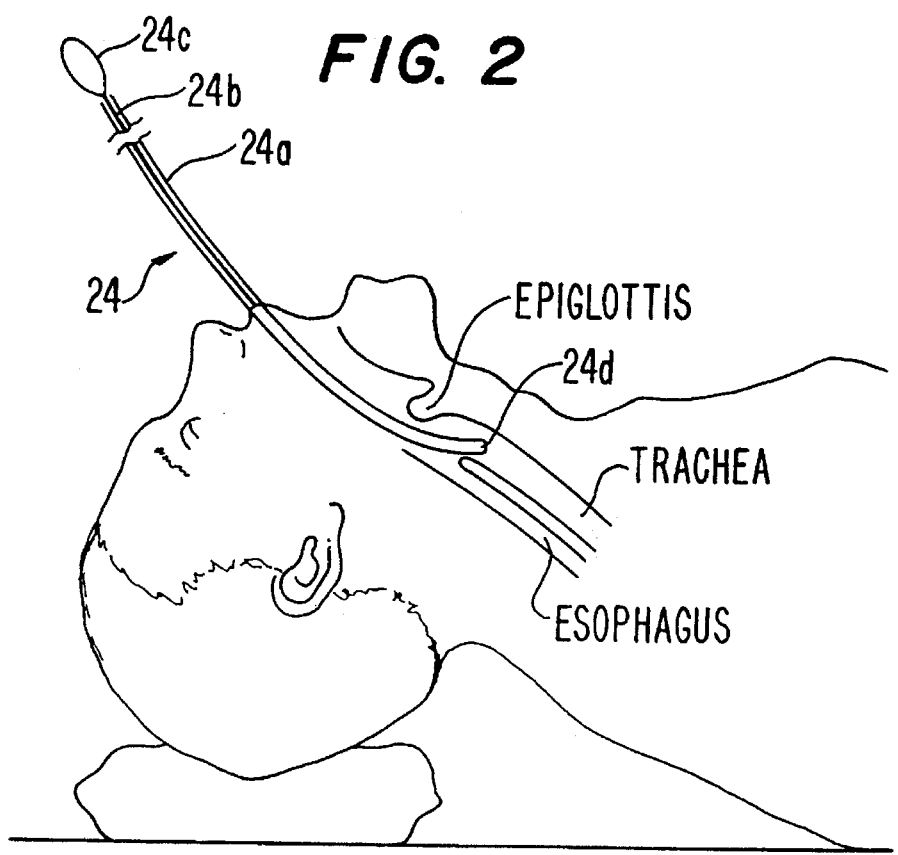
FIG. 2 is a schematic illustration of a patient during insertion of the introducer.

FIG. 2 shows a patient, without face mask, into whose mouth there has been placed the introducer 24 which is in the form of a flexible tube 24a preferably made of plastic and having inside it a removable reinforcing or stiffening element 24b, which was made of metal wire. The purpose of the wire 24b is to increase the rigidity of the plastic tube 24a during the insertion.

As shown in FIG. 2, one end of the reinforcing element 24b extends beyond one end of the flexible tube 24a to form a loop-shaped handle which allows withdrawal and insertion of element 24b from and into the tube 24a. The loop, which is preferably integral with the remainder of the reinforcing element, also serves as an abutment means for preventing the reinforcing element 24b from moving into a position where it would project outwardly from the other end of the tube, i.e., from that end which is inserted into the trachea, thus preventing contact between the wire element and the patient.

Element 24b is malleable so that when introducer is inserted into the flexible tube, as a whole can be bent into any desired configuration; this, in practice, will be one that allows the introducer to be best inserted into the trachea. The overall arrangement is such that the reinforcing element 24b provides the introducer as a whole with sufficient stiffness during insertion into the trachea whereas when the element 24b has been removed, the flexibility of the tube 24a is sufficient to allow the introducer, without the reinforcing element, to be easily placed between the face of the patient and the face mask when the same is placed on the patient.

As is also shown in FIG. 2, the leading end 24d of the introducer 24 has been moved past the patient's epiglottis and has just entered the upper end of the trachea.

In practice, the tubular introducer 24 will be inserted into the airway of the patient and such insertion will continue in anticipation that the introducer is actually inserted into the patient's trachea. After the introducer has been placed in what is believed to be the proper position, i.e., in the trachea, the reinforcing element is removed. The face mask is then placed on the patient's face, with the flexible tube 24a of the introducer being connected as shown in FIG. 1 and coming to lie between the patient's face and the face mask, and the patient is ventilated by the face mask.

In accordance with the present invention, the gas flowing out of the patient by way of the introducer is sampled, preferably continuously, for the purpose of determining the carbon dioxide content of the gas, thereby to obtain a determination of whether or not the end 24d of the introducer 24 has actually been placed into the patient's trachea. This is done by positioning the valve 20 into that position which places the introducer 24 into communication with the capnograph by way of the sampling line 26.

If the introducer has in fact been placed into the trachea, the capnograph will show a wave form having relatively large oscillations whereas if the introducer has been placed into the esophagus, the wave be generally flat or show only relatively small oscillations.

The following Table tabulates the capnograph measurements obtained as a consequence of an esophegeal and 33 tracheal placements:

TABLE I

| $CO_2$ Waveform Amplitude in mm Hg | Number of Esophageal Placements | Number of Tracheal Placements |
| --- | --- | --- |
| 0 | 29 | 0 |
| 1 | 2 | 0 |
| 2 | 3 | 0 |
| 3 | 2 | 0 |
| 4 | 0 | 0 |
| 5 | 1 | 0 |
| 6 | 0 | 0 |
| 7 | 1 | 0 |
| 8 | 1 | 0 |
| 9 | 0 | 0 |
| 10 | 0 | 0 |
| 11 | 0 | 0 |
| 12 | 0 | 0 |
| 13 | 0 | 0 |
| 14 | 1 | 0 |
| 15 | 0 | 0 |
| 16 | 0 | 0 |
| 17 | 0 | 0 |
| 18 | 0 | 0 |
| 19 | 0 | 0 |
| 20 | 0 | 0 |
| 21 | 0 | 0 |
| 22 | 0 | 1 |
| 23 | 0 | 1 |
| 24 | 0 | 1 |
| 25 | 0 | 3 |
| 26 | 0 | 1 |
| 27 | 0 | 5 |
| 28 | 0 | 4 |
| 29 | 0 | 7 |
| 30 | 0 | 6 |
| 31 | 0 | 1 |
| 32 | 0 | 0 |
| 33 | 0 | 1 |
| 34 | 0 | 1 |
| 35 | 0 | 1 |
| 36 | 0 | 2 |
| 37 | 0 | 0 |
| 38 | 0 | 1 |
| 39 | 0 | 0 |
| 40 | 0 | 1 |
| 41 | 0 | 1 |
| 42 | 0 | 1 |

As is apparent from the above Table, the carbon dioxide content of the gaseous medium which is obtained during ventilation when the introducer is placed in the trachea differs markedly from the carbon contents if the introducer is placed in the esophagus. Specifically, of the 79 capnograms tabulated above, carbon dioxide wave forms obtained during the 40 esophageal placements were well below 20 mm Hg, with the 29 being flat or 0, as compared to the carbon dioxide wave forms obtained during the 39 tracheal placements, each of which was above 20 mm Hg, with about half of them being in the 27 to 30 mm Hg range.

Thus, the anesthesiologist is readily able to ascertain whether or not the introducer has in fact been placed correctly, i.e., in the trachea. If it has, the next step is to pass the endotracheal tube (not shown) over the introducer until the endotracheal tube has been inserted into the patient's trachea. The introducer is then withdrawn and ventilation is continued through the endotracheal tube.

If, however, the carbon dioxide measurement indicates that the end of the introducer has been inserted into the esophagus, the tube 24a is at least partially withdrawn and is disconnected from the configuration shown in FIG. 1, the reinforcing element 24b is reinserted into tube 24a, and the thus reinforced introducer 24 is reinserted into what is now once again anticipated to be the trachea. This procedure is continued as described above, i.e., the carbon dioxide level of the gas flowing out of the introducer is again measured to determine whether or not its end has actually been placed in the patient's trachea. This step and the partial withdrawal and reinsertion of the introducer, are continued as often as necessary, until the carbon dioxide measurement indicates that the end of the introducer has in fact been inserted into the trachea, whereupon the endotracheal tube is inserted into the patient in the manner described above.

It will be understood that the above description of the present invention is susceptible to various modifications, changes and adaptations, and the same are intended to be comprehended within the meaning and range of equivalents of the appended claims.

What is claimed is:

1. A method of intubating and ventilating a patient to be anesthetized, comprising the steps of:
   (a) inserting a tubular introducer into the airway of the patient and continuing such insertion in anticipation that the insertion will continue until the introducer is inserted into the trachea of the patient;
   (b) ventilating the patient by face mask;
   (c) sampling gaseous medium flowing out of the introducer during masked ventilation of the patient for measuring the carbon dioxide content of the gaseous medium thereby to obtain a determination of whether or not the end of the introducer has actually been inserted into the trachea of the patient; and
   (d) if the carbon dioxide measurement indicates that the end of the introducer has actually been inserted into the trachea, passing an endotracheal tube over the introducer into the trachea of the patient, withdrawing the introducer and continuing ventilation through the endotracheal tube, or
   (e) if the carbon dioxide measurement indicates that the end of the introducer has not been inserted into the trachea, at least partially withdrawing the introducer and reinserting it into what is again anticipated to be the trachea and thereafter repeating step (c) and said at least partial withdrawal and reinsertion, as often as necessary, until the carbon dioxide measurement does indicate that the end of the introducer has in fact been inserted into the trachea and then proceeding with step (d).

2. The method defined in claim 1, wherein the sampling is carried out continuously.

3. In a method of intubating and ventilating a patient to be anesthetized, comprising the steps of:
   (a) inserting into the airway of the patient an introducer in the form of a flexible tube having inside it a removable reinforcing element which provides the introducer with sufficient stiffness during insertion and continuing such insertion in anticipation that the insertion will continue until the introducer is inserted into the trachea of the patient;
   (b) removing the reinforcing element from the introducer, applying a face mask to the face of the patient with the flexible tube of the introducer lying between the face mask and the face of the patient, and ventilating the patient by face mask;
   (c) sampling gaseous medium flowing out of the introducer during masked ventilation of the patient for measuring the carbon dioxide content of the gaseous medium thereby to obtain a determination of whether or not the end of the introducer has actually been inserted into the trachea of the patient; and
   (d) if the carbon dioxide measurement indicates that the end of the introducer has actually been inserted into the trachea, passing an endotracheal tube over the introducer into the trachea of the patient, withdrawing the introducer and continuing ventilation through the endotracheal tube, or
   (e) if the carbon dioxide measurement indicates that the end of the introducer has not been inserted into the trachea, at least partially withdrawing the introducer, re-inserting the reinforcing element and re-inserting the reinforced introducer into what is again anticipated to be the trachea and thereafter repeating step (c) and said at least partial withdrawal and reinsertion, as often as necessary, until the carbon dioxide measurement does indicate that the end of the introducer has in fact been inserted into the trachea and then proceeding with step (d).

4. The method defined in claim 3, wherein the sampling is carried out continuously.

5. An introducer for facilitating placement of an endotracheal tube into a patient's trachea comprising:
   a flexible tube for sampling gaseous medium flowing therethrough from a patient during masked ventilation; means including a removable reinforcing element which is inserted into said flexible tube for providing stiffness for aiding in placement of said flexible tube into a patient's trachea; said flexible tube in combination with said removable reinforcing element providing means for facilitating placement of an endotracheal tube into a patient's trachea; means for removing said reinforcing element from said flexible tube thereby rendering said flexible tube unobstructed to allow sampling of gaseous medium from a patient flowing therethrough; said flexible tube, responsive to the removal of said reinforcing element being sufficiently flexible to enable said flexible tube to lie between a face mask and a patient's face while continually providing means for sampling gaseous medium flowing therethrough during ventilation of a patient via a face mask.

6. An introducer as defined in claim 5, wherein said reinforcing element is malleable thereby to allow the introducer, when said reinforcing element is inserted in said flexible tube, to be bent into any desired configuration.

7. An introducer as defined in claim 5, wherein said reinforcing element extends beyond an end of said tube to form a handle which constitutes said means for removing said reinforcing element from said flexible tube.

8. An introducer as defined in claim 5, wherein said handle is configured in the form of a loop.

9. An introducer as defined in claim 5, wherein said reinforcing element extends beyond one end of said tube and carries abutment means for preventing said reinforcing element from moving into a position where it would project outwardly from the other end of said tube.

10. An introducer as defined in claim 9, wherein said abutment means is in the form of a handle which constitutes said means for removing said reinforcing element from said flexible tube.

11. An introducer as defined in claim 9, wherein said handle is integral with the remainder of the said reinforcing element.

12. An introducer as defined in claim 11, wherein said handle is configured in the form of a loop.

13. An introducer as defined in claim 5, wherein said flexible tube is made of plastic.

* * * * *